(12) United States Patent
Belli et al.

(10) Patent No.: US 6,173,608 B1
(45) Date of Patent: Jan. 16, 2001

(54) DEVICE FOR MEASURING FORCES EXERTED DURING AMBULATORY EXERCISE

(75) Inventors: Alain Belli, Saint Etienne; Antoine Berger, Roche la Moliere, both of (FR)

(73) Assignee: Centre Stephanois de Recherches Mechaniques Hydromecanique et Frottement S.A., Andrezieux Boutheon (FR)

(*) Notice: Under 35 U.S.C. 154(b), the term of this patent shall be extended for 0 days.

(21) Appl. No.: 08/875,628

(22) PCT Filed: Jan. 31, 1996

(86) PCT No.: PCT/FR96/00162
§ 371 Date: Oct. 3, 1997
§ 102(e) Date: Oct. 3, 1997

(87) PCT Pub. No.: WO96/24286
PCT Pub. Date: Aug. 15, 1996

(30) Foreign Application Priority Data
Feb. 8, 1995 (FR) .................................................. 95 01692

(51) Int. Cl.⁷ ............................ G01M 19/00; A61B 5/00; A61B 5/103; A61B 5/117
(52) U.S. Cl. ............................................. 73/172; 600/595
(58) Field of Search ................................ 600/595; 73/172

(56) References Cited

U.S. PATENT DOCUMENTS

| 5,229,454 | 7/1993 | Weichmann . |
| 5,299,454 | * 4/1994 | Fuglewicz et al. .................... 73/172 |
| 5,360,015 | * 11/1994 | Heurte ................................. 128/779 |
| 5,475,087 | * 12/1995 | Nashner ............................... 128/782 |
| 5,476,013 | * 12/1995 | Nashner ............................... 128/782 |
| 5,623,944 | * 4/1997 | Nashner ............................... 128/779 |

FOREIGN PATENT DOCUMENTS

| 90 17 709 | 9/1991 | (DE) . |
| 0603115A2 | 6/1994 | (EP) . |
| 93/06779 | 4/1993 | (WO) . |
| WO 93/06779 | * 4/1993 | (WO) ........................... A61B/5/103 |

* cited by examiner

*Primary Examiner*—Hezron Williams
*Assistant Examiner*—Dennis Loo
(74) *Attorney, Agent, or Firm*—Wall Marjama & Bilinski

(57) ABSTRACT

A device for measuring the forces exerted by each leg, particularly during ambulatory activity, including at least one assembly provided with a powered treadmill in a frame consistency of a rigid structure engaging the various portions of the treadmill for drawing the treadmill. The rigid structure is supported by force measuring sensors secured to a common ground-engaging plane for measuring vertical and tangential forces.

7 Claims, 3 Drawing Sheets

DEVICE FOR MEASURING FORCES EXERTED DURING AMBULATORY EXERCISE

FIELD OF THE INVENTION

The invention relates to the technical field of analysis and measurement apparatus for biomechanical medical purposes, especially medical and sporting use.

BACKGROUND OF THE INVENTION

In the event of rehabilitation following any injury or simply in order to monitor and test an individual, it is important to ascertain the forces exerted by each of the legs when walking normally.

Apparatus is known which can be used to measure angular variations between the tibia and femur corresponding, in particular, to movements of flexion and extension when walking. In contrast, such apparatus provides no indication of the forces exerted by the foot.

In order to measure forces exerted by the foot, there are known systems which use a platform which rests on the floor and uses sensors. The platform is located along the path that is walked in order to obtain an image of the force exerted by a footstep. Nevertheless, it appears that such a solution is not satisfactory given the fact that the person has a natural tendency to pause before walking onto the platform so that the force which is exerted is not natural. This system can be duplicated for each leg. This system is not suitable for the measurement of several consecutive steps.

A proposal has also been made to equip endless belts in an attempt to measure the loads applied when an individual walks. This system involves fitting force meters between the base over which one side of the endless belt travels and the chassis. Such a solution has several drawbacks:

First the measurement cannot differentiate between the force exerted by each leg; this poses relatively few problems when analysing running motion because both feet practically never touch the ground simultaneously since contact is essentially one-footed but it is an important shortcoming when the individual is walking because both feet always touch the ground since contact is two-footed, Second it is impossible to measure tangential forces.

Patent EP-A-0603115 and the Publication BIOMEDIZ-INISCHE TECHNIK, Volume 32, No. 10, October 1987 disclose solutions whereby the endless belt consists of two separate parts. In Patent EP-A-0603115, separation is transversal whereas in the Publication BIOMEDIZINISCHE TECHNIK, separation is longitudinal. This being so, in both cases the sensors are placed between the belt and the base, i.e. the part over which the belts travel. It therefore seems that these solutions cannot be used to measure tangential forces taking into account the friction of the belts on the base.

The invention aims to overcome these drawbacks in a simple, safe, effective and rational manner.

The problem which the invention aims to solve is to provide physiologists and orthopaedists with a solution capable of measuring vertical and horizontal forces, i.e. tangential forces of footsteps, especially for several successive steps by advantageously, but not exhaustively, differentiating between the forces exerted by the right leg and those exerted by the left leg.

SUMMARY OF THE INVENTION

In order to solve this problem, a device for measuring the forces exerted by each leg in particular when walking has been devised and perfected which comprises at least one assembly equipped with a motor-driven endless belt installed in a chassis consisting of a rigid structure that accommodates the various drive elements of the belt, said structure being supported by force meters that are physically connected to a common floor support plate in order to measure the vertical and tangential forces.

The vertical and tangential forces are therefore measured given the fact that friction is totally eliminated because the part that accommodates the endless belt is isolated from the floor.

Under these conditions, the friction forces of the belt on its mounting and of all the elements that drive the belt are internal forces and are not applied to the force meters that support the structure under any circumstances.

In order to solve the problem of measuring the various forces exerted by each of the legs during several consecutive steps while walking, the device comprises two independent assemblies arranged in parallel side by side corresponding to each leg, each of the assemblies being separately monitored by force meters supported by the common floor support plate.

Advantageously, each of the structures comprises an upper part in the form of a straight beam designed for mounting an endless belt installed in combination with drive rollers fixed at each of the ends of said beam, said structures being placed opposite each other so as to position the belts so that they almost abut but prevent any contact between the two belts.

In order to solve the problem of measuring vertical and tangential forces straightforwardly and obtaining precise access to rapid variation of these forces, the force meters can be crystal-type force meters capable of measuring the three orthogonal components of a dynamic force acting in any direction.

Advantageously the force meters are attached to each of the ends of each chassis.

BRIEF DESCRIPTION OF THE DRAWINGS

The invention is explained below in greater detail, reference being made to the accompanying drawings in which.

DETAILED DESCRIPTION OF THE INVENTION

Figure 1:
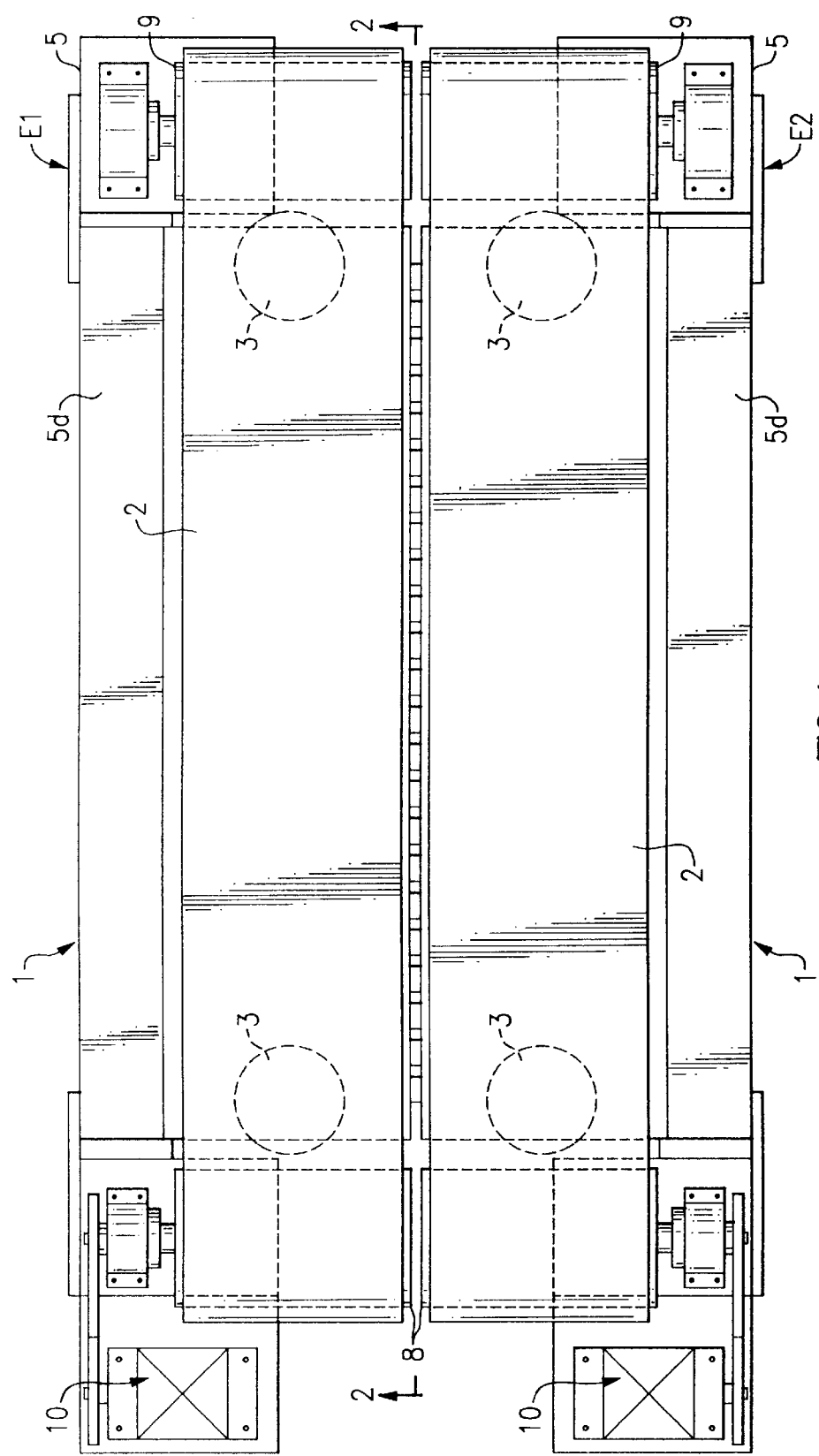
FIG. 1 is a top view of the device.
Figure 2:
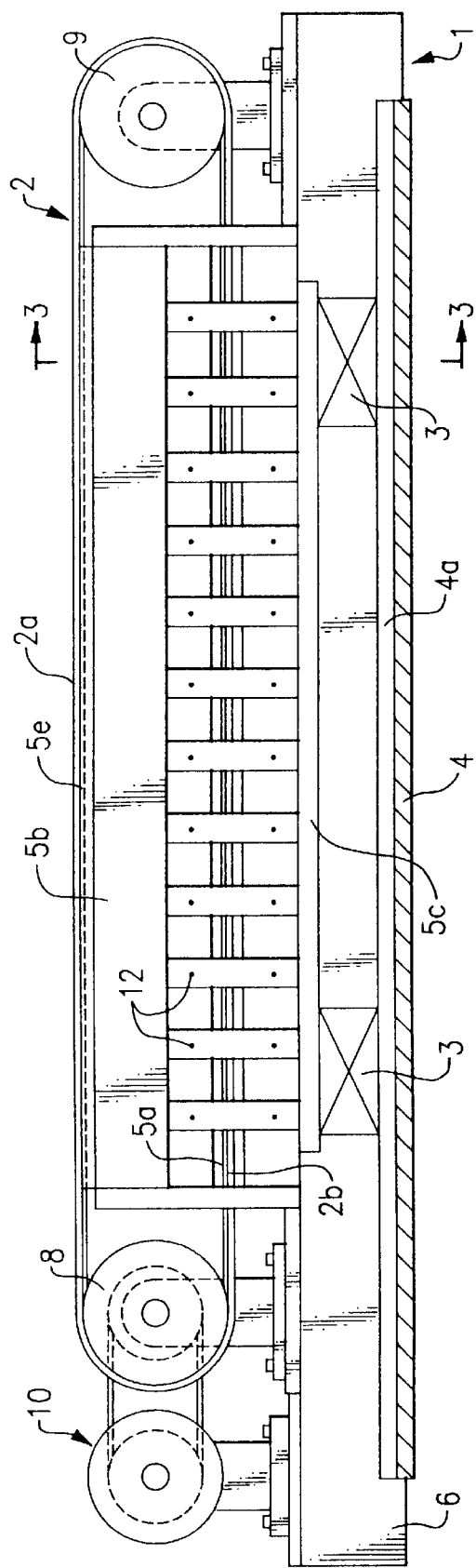
FIG. 2 is a longitudinal cross-sectional view along line 2.2 in FIG. 1.
Figure 3:
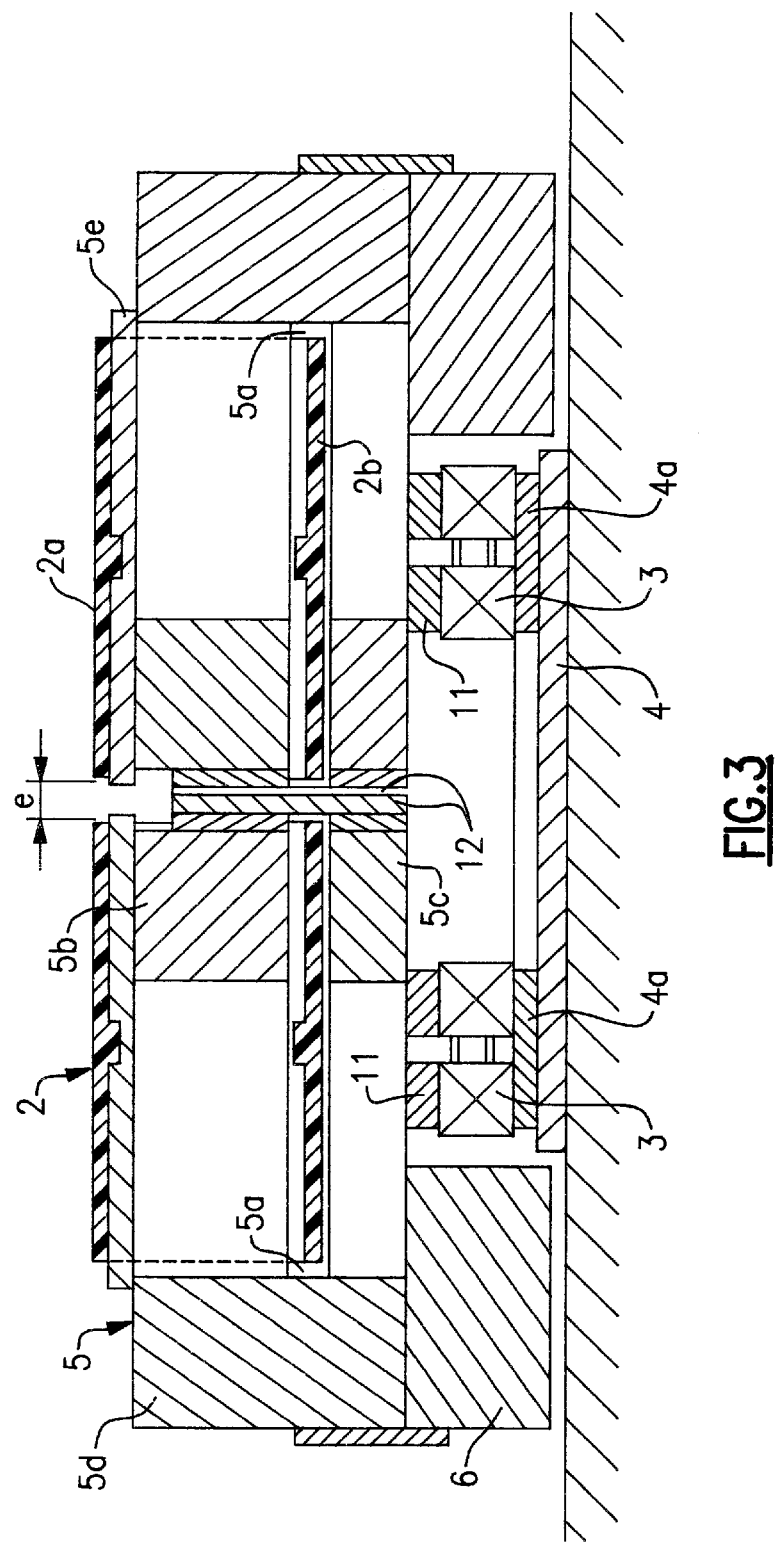
FIG. 3 is a transverse cross-sectional view along line 3.3 in FIG. 2.

According to the invention, the device comprises two independent assemblies (E1) and (E2) arranged in parallel side by side. Each assembly (E1) and (E2) constitutes a support chassis (1) devised for installing a motor-driven endless belt (2).

Each of the chassis (1) is monitored by force meters (3) mounted on a common floor support plate (4).

According to the invention, each of the chassis is designed to constitute a rigid structure that is isolated in space in order to make it possible to effectively measure vertical and tangential forces in combination with force meters (3) completely independently of friction. In the embodiment shown, each of the structures comprises an upper part in the form of a straight beam (5) having a slit (5a) to allow clearance of one side (2a) of the endless belt (2).

The upper side (2a) of the belt (2) rests on a plate or base (5e) of which the surface which comes into contact with the belt is treated in order to reduce friction.

The beam (5) may be of one-piece construction or consist of two parallel members (5b) (5c) which form slit (5a), the members being joined two at a time by a lateral member (5d). Beam (5), regardless of the embodiment, may also be joined at the level of its lower surface and on the side of its external arm to another member (6) essentially having the function of further increasing the rigidity of beam (5). In addition, member (6) projects beyond the transverse sides of beam (5) and may have mounting feet (7) in order to install the drive rollers (8) and (9) of the belt (2).

In a conventional manner, one of the rollers (8) is motor driven for example. Roller (8) may have an integral motor or be connected by any known, appropriate means to an independent motor (10) so as to drive each of the belts (2) in a direction that is opposed to the direction of walking.

The chassis assembly as defined rests on floor support plate (4) with the force meters (3) in between them. For instance, the lower side of each of the beams (5) has a precision-ground rail (11) to which one of the ends of the force meters (3) is attached. The other end of the force meters is attached to parallel rails (4a) of the common floor support plate (4).

Both the chassis are absolutely identical and are arranged opposite each other in parallel and are joined to the common floor plate (4) via the force meters (3) leaving a very small gap (e) between them. As a result, the endless belts (2), when installed on the corresponding drive rollers (8) and (9), are independent but almost abut.

In order to measure the forces independently, especially the tangential forces, it is crucial that each of the belts is driven by an independent motor.

As far as the force meters (3) are concerned, the latter advantageously consist of crystal-type force meters capable of measuring the three orthogonal components of a dynamic or quasi static force acting in any direction. Advantageously, these force meters may be of the same type as those distributed by the company KISTLER INSTRUMENTS.

These constructional features therefore make it possible to separate the right leg from the left leg and, consequently, allow independent measurement of the vertical and tangential forces corresponding to two-footed contact that is obtained when walking.

Obviously, the entire device as described is connected to any system for processing and analysing the measurements made in a known manner.

Provision is also made to link the two parallel members (5b) (5c) using plurality of short vertical bars (12), spaced at intervals. Note that the short bars for making the beams of both the opposite assemblies rigid are attached two by two at regular alternate intervals in order to reduce the space between said two beams after joining them to the common floor support plate in combination with the force meters.

Without extending beyond the scope of the invention, provision is made to connect a chassis suitable for accommodating a single motor-driven endless belt rather than independent belts each corresponding to one leg. In this case the essential application of the device is to measure forces where an individual is running when contact is essentially of the one-footed type.

The advantages are clearly apparent from the description, the following aspects being emphasised and restated in particular:

the possibility of independently measuring the vertical and tangential forces exerted by each of the legs when walking, ease of manufacture, the effectiveness of the result obtained and its high accuracy, measurement being totally independent of friction and the mechanical drive forces of the belts.

What is claimed is:

1. A device for measuring the forces exerted by each leg of an individual when walking and running, said device comprising:

a chassis;

at least one assembly equipped with an endless belt assembly installed in said chassis;

drive means for driving said endless belt assembly, said at least one assembly equipped with the endless belt assembly including a rigid structure which accommodates said drive means and said endless belt assembly; and a plurality of force measuring sensors disposed entirely beneath said endless belt assembly, said rigid structure being supported by said force measuring sensors secured to a common floor support plate, allowing said force measuring sensors to measure both vertical and tangential forces exerted by each leg of an individual.

2. A device according to claim 1, including two assemblies installed in said chassis and arranged in parallel in a side by side relation to independently match each leg of an individual using said device, each said assembly being separately mounted by said plurality of force measuring sensors secured to said common floor support plate.

3. A device according to claim 2, wherein each independent assembly includes an endless belt, said device including drive means for driving each endless belt in a direction opposite in direction to a walking direction, each belt being installed in said chassis.

4. A device according to claim 3, wherein each independent assembly includes a rigid structure, including an upper part on the form of a straight beam having means for installing and supporting said endless belt therein, said drive means including drive rollers attached to ends of said beam, said structure being arranged opposite each other so as to position said endless belts in proximate parallel relation such that said belts nearly abut but do not touch each other.

5. A device according to claim 4, wherein each said beam includes two parallel members forming a slit allowing clearance of one side of a supported endless belt, said members being joined by at least one lateral member, said bemas each including a rigidity member having means for mounting said drive rollers thereto.

6. A device according to claim 1, wherein said force-measuring sensors are crystal-type sensors capable of measuring the three orthogonal components of a rapidly varying dynamic force acting in any direction.

7. A device according to claim 2, wherein said force-measuring sensors are fixedly mounted to ends of said chassis.

* * * * *